United States Patent [19]

Schönmann et al.

[11] Patent Number: 4,772,472

[45] Date of Patent: Sep. 20, 1988

[54] FORMED OR MOLDED BODY AND METHOD AND APPARATUS FOR MANUFACTURING SUCH BODY

[75] Inventors: Holger Schönmann; Hans P. Eck, both of Eberbach/Baden, Fed. Rep. of Germany

[73] Assignee: R. P. Scherer GmbH, Eberbach, Fed. Rep. of Germany

[21] Appl. No.: 285

[22] Filed: Jan. 2, 1987

[30] Foreign Application Priority Data

Jan. 3, 1986 [DE] Fed. Rep. of Germany ....... 3600084

[51] Int. Cl.$^4$ ............................................. A61M 31/00
[52] U.S. Cl. ................................... 424/451; 424/455; 424/456; 424/457
[58] Field of Search ....................... 220/8, 20; 206/528; 424/400, 451, 456, 457, 455; 604/892.1

[56] References Cited

U.S. PATENT DOCUMENTS

| | | | |
|---|---|---|---|
| 1,419,618 | 6/1922 | Demins | 424/451 |
| 4,350,271 | 9/1982 | Eckenhoff | 604/892.1 |

FOREIGN PATENT DOCUMENTS

| | | | |
|---|---|---|---|
| 1492077 | 6/1969 | Fed. Rep. of Germany | 424/457 |
| 0206515 | 1/1983 | Japan | 424/455 |
| 2099698 | 5/1982 | United Kingdom | 424/451 |

Primary Examiner—John E. Kittle
Assistant Examiner—Patrick J. Ryan
Attorney, Agent, or Firm—Gilbert L. Wells

[57] ABSTRACT

A formed or molded body, a manufacturing method and a manufacturing apparatus therefor, wherein several equal or different active ingredients in suitable, equal or different carrier substances are filled at the same time side-by-side without a partition into a uniform enclosure or envelope to provide a formed or molded body with uniform outer appearance and with separate inner regions.

10 Claims, No Drawings

FORMED OR MOLDED BODY AND METHOD AND APPARATUS FOR MANUFACTURING SUCH BODY

The invention relates to a formed or molded body with an enclosure or envelope of polymer material, gelatine or the like, and with a filling in the enclosure or envelope. Generally, the envelope may be a hard or soft gelatine capsule that is filled with pharmaceutical preparations. The invention also relates to a method for manufacturing such formed or molded bodies as well as to a corresponding apparatus suitable for manufacturing the molded bodies and for carrying out the method, respectively.

For manufacturing soft gelatine capsules the so-called rotary-die-method has substantially been successful, in which method gelatine bands are guided over forming rollers provided with hollow form recesses or dies and the gelatine bands are introduced between these forming rollers. By means of a filling block in the form of a gore or gusset the gelatine bands are pressed into the mold cavities or dies, and on the other hand at the same time the filling substance is injected into the thus formed capsules. Thus, the soft capsules are manufactured and filled in one working step. Thereby, only one uniform substance or a homogeneous substance mixture, i.e. a mixture of several substances, can be filled into the capsules.

Further, hard gelatine capsules are known which are plugged together telescopically from two pre-fabricated capsule parts. Prior to the plugging together, in a separate working step a uniform substance or a homogeneous substance mixture or in several working steps one after the other different layers of substances or substance mixtures are filled into the capsule main body. The manufacturing of such telescoping capsules is, thus, technically more complicated and more expensive than the manufacturing of soft gelatine capsules. In using several different layers of filling substances for hard gelatine capsules care must be taken that the substances are compatible with each other and that a mixing or mingling of the substances after the filling is permissible.

It is an object of the invention to provide a formed or molded body, a manufacturing method as well as a manufacturing apparatus therefor, by which it is possible to fill different substances or substance mixtures defining phases and even such substances which are not compatible with each other or which would prematurely react with each other, in one operating step into one and the same molded body such that within that molded body regions of different phases are permanently present.

The formed or molded body according to the invention is characterized in that the filling comprises at least two equal active ingredients in two different carrier substances (phases) or at least two different active ingredients in two equal carrier substances (phases), and that the carrier substances (phases) are provided in the enclosure or envelope layered side-by-side without a partition or separating wall.

Accordingly, a method for manufacturing such a formed or molded body according to the invention is characterized in that at least two active ingredients with their associated carrier substances are introduced or filled at the same time into different regions of a common enclosure or envelope and are brought into contact with each other at at least one interface.

Thus, by the invention a formed or molded body as well as manufacturing method suitable therefor are provided wherein by simultaneous filling of several substances it is possible to introduce into one single molded body or capsule two or more layered, equal or different phases. Thereby, it is possible on the one hand to accomodate equal active ingredients embedded in different carrier substances or matrices in one and the same envelope as a dose unit in such a manner that for example with pharmaceutical products different resorption velocities can be obtained in the body. On the other hand it is possible to accomodate different active ingredients, which are not compatible with each other or which would intermix with each other in an undesired manner, without a mutual reaction or intermixing by means of equal or different carrier substances or phases side-by-side without partition in a common enclosure or envelope. Thereby the carrier substances or phases form a stable matrix in their associate partial region within the envelope, whereby also a cross linkage of the carrier substances or a solidification of fillings introduced in a liquid state is possible within the envelope. The carrier substances can be used, if it is only secured that an exchange or a reaction or interaction between the active ingredients in the different regions is excluded or a diffusion at the interfaces between the different regions only takes place very slowly or during long time periods.

By filling the substances in separate regions of a uniform molded body for example the following advantages can be achieved:

With medicines contained in a gelatine capsule filled with two different, incompatible, medically active substances in at least two equal or different carrier substances there is provided a chemical stabilisation of different active ingredients, which are incompatible with each other and which would react on contact with each other, such that they can be stored in one and the same dose unit practically as desired and an interaction of the reactive substances is avoided up to the time at which the molded body is taken by a patient. Only after being taken and after the envelope has been dissolved the active ingredients can then interact with each other.

With a molded body with the features of a gelatine capsule filled with two equal, medically active substances in different carrier substances that are compatible with each other a different resorption of equal or different substances from one and the same molded body can be achieved, whereby for example the active ingredients can become effective in the body of the patient one after the other at the same or different locations.

If after the manufacturing of the filled molded body a certain matrix is formed therein, by the interaction of different matrices the contents of the capsule can still be influenced later to become effective in a retarding manner. Thus, in filling active ingredients that react in a cross-linking manner with the material of the envelope, for example the gelatine, it is possible to form within a single dose, constituted by the molded body, regions that do not cross-link with each other, so that when the envelope is decomposed, opened or disintegrated within the body of the patient, different partial doses are ensured after a certain time or within a predetermined time period, which partial doses can have special therapeutic effects. Thereby, within one and the same molded body, regions of different solubility can be provided, for instance also in that parts of the envelope are soluble in water or body fluids and other parts of the envelope are scantily soluble or insoluble in the same media, whereby the possibilities of interaction between envelope and/or active ingredient and/or carrier substance are multiplied. Altogether one obtains an improvement in the possibilites for presenting medicines, whereby physical or chemical incompatibilities of the active ingredients can be controlled properly and separately. The active ingredients after filling can also be contained in the common envelope in a manner similar to a sponge and can be released therefrom only slowly.

The carrier substances forming the respective matrix can be lipophil and thus for example can consist of oils, waxes or greases with which the active ingredients are able to be mixed or in which they are soluble. The carrier substances can also be hydrophil, i.e. formed on the basis of water, as for example poly-glycols, whereby the active ingredients are mixed, suspended or solved in these media.

The apparatus according to the invention for manufacturing the described formed or molded bodies and for carrying out the manufacturing method requires only slight modifications as compared to known capsule manufacturing machines. Substantially, instead of previously one station for supplying the filling medium now a corresponding plurality of such stations is needed. In a manufacturing machine for soft capsules working according to the so-called "rotary-die-method", thus, two or more supply channels or conduits for the filling medium with a corresponding number of injection nozzles are provided which terminate in one and the same mold cavity that consists of the two form halves of the two forming rollers. Apart from that it is only necessary to redesign the very precisely working supply mechanism such that the filling of different solutions or mixtures is possible in a precise manner also with different viscosities. Thereby not only equal but also different filling substances (equal and/or different active ingredients, equal and/or different carrier substances) can be supplied. Thereby, for example, also components which normally cannot be mixed with each other and which up to now could not be filled in one single working step can now be supplied to introduced into a uniform molded body without a partition in a very precisely dosed manner. According to the state of the art up to now it was only possible to fill pre-mixed homogeneous substances in a dosed manner into a molded body, whereby care had to be taken that the substances did not react with each other already during the supply or during the filling or during the storage of the molded bodies. Thus, up to now, it was also not possible to let the active ingredients become effective in the body of a patient one after the other. In many cases a reaction of the different substances occurred already in the store tank or in the supply conduit in front of the filling station so that it was not possible to fill certain substances. By the separate supply and by the separate, however simultaneous introduction or filling into one uniform molded body these problems can be avoided.

We claim:

1. In a formed body having an enclosure of polymer material and a filling inside said enclosure, the improvement comprising said filling comprising:
   at least first and second equal active ingredients in first and second different liquid carrier substances said active ingredients mixed with said carrier substances and defining at least two phases, said phases positioned in said enclosure in a layered manner side-by-side without a partition between said phases.

2. The formed body of claim 1, wherein said enclosure is a gelatine capsule.

3. The formed body of claim 1, wherein parts of said enclosure are soluble in water and other parts of said enclosure are insoluble in water.

4. The formed body of claim 1, wherein said first liquid carrier substance is selected from the group consisting of oils, waxes and greases and said second liquid carrier substance is selected from the group consisting of water and poly-glycols.

5. The formed body of claim 1, wherein said first liquid is lipophilic and said second liquid is hydrophilic.

6. In a formed body having an enclosure of polymer material and a filling inside said enclosure, the improvement comprising said filling comprising:
   at least first and second different active ingredients in first and second equal liquid carrier substances said active ingredients mixed with said carrier substances and defining at least two phases, said phases positioned in said enclosure in a layered manner side-by-side without a partition between said phases.

7. The formed body of claim 6, wherein said enclosure is a gelatine capsule.

8. The formed body of claim 6, wherein parts of said enclosure are soluble in water and other parts of said enclosure are insoluble in water.

9. In a method for manufacturing a formed body having a common enclosure of polymer material and a filling inside said enclosure, the improvement comprising:
   introducing at least first and second phases into different regions of said common enclosure and bringing said phases into contact with each other at at least one interface, each of said phase defined by a mixture of an active ingredient and an associated liquid carrier.

10. The method of claim 9, wherein said first phase is introduced through a first conduit and said second phase is introduced through a second conduit.

* * * * *